United States Patent [19]

Saotome

[11] 4,230,694
[45] Oct. 28, 1980

[54] PROCESS FOR PREVENTION OF PLANT INFECTIONS CAUSED BY SCATTERED SPORES AND COMPOSITION

[76] Inventor: Kiyoshi Saotome, 2-4-10, Setagaya, Setagaya-ku, Tokyo, Japan

[21] Appl. No.: 949,852

[22] Filed: Oct. 10, 1978

Related U.S. Application Data

[63] Continuation-in-part of Ser. No. 798,033, May 18, 1977, abandoned, which is a continuation-in-part of Ser. No. 630,889, Nov. 11, 1975, abandoned.

[51] Int. Cl.³ .................... A01N 27/00; A01N 61/02
[52] U.S. Cl. .................................. 424/172; 424/355
[58] Field of Search ............................. 424/172, 355

[56] References Cited

U.S. PATENT DOCUMENTS

| 896,335 | 8/1908 | Stokes | 424/355 |
|---|---|---|---|
| 2,162,904 | 6/1939 | Allison | 424/355 |
| 3,199,944 | 8/1965 | Gabor et al. | 71/121 |
| 3,388,992 | 6/1968 | Ratledge | 71/127 |
| 3,410,678 | 11/1968 | Ratledge | 71/127 |

FOREIGN PATENT DOCUMENTS

| 4719024 | 2/1971 | Japan | 424/355 |
|---|---|---|---|
| 430024 | 6/1935 | United Kingdom | 424/355 |

Primary Examiner—Allen J. Robinson
Attorney, Agent, or Firm—Wenderoth, Lind & Ponack

[57] ABSTRACT

Process for protecting plants from diseases caused by airborne carriers by application of a stable W/O paraffin emulsion. The emulsion is produced by emulsifying a hard paraffin having substantially the same number of carbon atoms naturally present on said plants with a $C_{12}$-$C_{18}$ fatty acid soap under conditions such as to yield an emulsion particle size of 1 to 5 microns.

13 Claims, No Drawings

PROCESS FOR PREVENTION OF PLANT INFECTIONS CAUSED BY SCATTERED SPORES AND COMPOSITION

This is a continuation-in-part of Ser. No. 798,033 filed May 18, 1977 abandoned, which in turn is a continuation-in-part of Ser. No. 630,889, filed Nov. 11, 1975, now abandoned.

BACKGROUND AND PRIOR ART

This invention relates to the protection of plants from diseases caused by airborne carriers, e.g. spores, bacteria, etc. by application of a W/O emulsion of a block-like paraffin film having substantially the same number of carbon atoms as is naturally present on the surface of the plant.

The naturally occurring paraffin layer of most plants is inadequate to prevent transpiration and attack by micro-organisms, spores and the like.

It is generally known to apply paraffin films to plants for the purpose of preventing transpiration and attack by microorganisms.

These films were not entirely satisfactory due to the fact that the paraffin employed was phytotoxic or incompatible with that naturally present on the plant surface. Moreover, these paraffins were applied to the plant surface as an emulsion and the emulsifier employed often caused the resulting paraffin film to be incompatible with the natural paraffin film on the plant surface.

A significant advance in this area was disclosed in applicant's Japanese Pat. No. 46-4964 which utilized an emulsion of a paraffin having the same number of carbon atoms as that naturally present on the plant and employed fatty acid emulsifiers.

However, because of the manner in which the emulsion in Japanese Pat. No. 46-4964 was prepared, the colloidal particles in the emulsion were as large as 5 to 10 microns.

In this regard, the emulsion of the Japanese patent is prepared by a batch process which involves heating paraffin and fatty acid soap emulsifier to about 90° to 100° C. under stirring to form a solution. When the hot emulsion is permitted to cool, i.e. in a cooling bath, the colloidal particles of paraffin tend to crystallize on the walls of the container but remain in solution in the internal portion of the container. As the batch is stirred, the crystallized paraffin tends to the entire batch is cooled to about 40° C., the particles of paraffin are crystallized and stabilized at a particle size of above 5 microns, i.e. up to 10 microns.

An emulsion containing such large particles is not economical because it will not retain its efficacy when diluted with water, e.g. to a 200x dilution.

OBJECTIVES AND BRIEF DESCRIPTION OF THE INVENTION

Accordingly, it is an objective of this invention to provide a method for prevention of airborne diseases in plants by the use of a paraffin emulsion which is effective at high dilutions with water.

It is also an objective of this invention to produce an emulsion for use in the above method.

It is a further objective to provide a paraffin coating which is compatible with the plant being treated in terms of lack of phytotoxicity and long term retention of the coating on the plant.

It is a yet further objective to provide a coating which has low mammalian toxicity.

BRIEF DESCRIPTION OF THE INVENTION

These and other objectives are met by the present invention wherein a spore-resistant protective layer is formed on plants by applying a W/O emulsion of a hard paraffin of about the same number of carbon atoms as the paraffin naturally present on the surface of the plant being treated. The emulsion is produced by emulsifying the paraffin with a $C_{12}$ to $C_{18}$ fatty acid soap under conditions such as to produce an emulsion particle size of 1 to 5 microns.

After the emulsion is suitably diluted with water, e.g. 200x and sprayed on the plant to be protected and the moisture evaporates from the emulsion, a highly tenacious paraffin film of about 0.8 and 1 micron is formed on the plant. Such film provides excellent protective effects against airborne diseases.

In consequence, the airborne spores of various microorganisms, instead of adhering to the plant, adhere to the paraffin film and insertion of germinating tubes by said spores into the plant, e.g. stomata of its leaves is physically impossible. Thus propagation of said spores is inhibited.

DETAILED DESCRIPTION OF THE INVENTION

A paraffin selected from those having between 20 and 35 carbon atoms, i.e. between $C_{20}H_{42}$ and $C_{35}H_{72}$ can attain the above objectives, however, a paraffin of between $C_{20}H_{42}$ and $C_{25}H_{52}$ and having a melting point of 36.8° C. to 74.7° C. is preferred because it is similar to the natural paraffin on the surface of many plants.

It is preferred that the paraffin be at least 80% n-paraffin since n-paraffins are the predominant isomer naturally present on the plants.

When the carbon chain of the paraffin contains less than 20 carbon atoms, such paraffin is undesirable because it melts and becomes oily, thereby blocking the stomata of the plant. This, in turn, causes lesions.

When the paraffin has a carbon length greater than that of the paraffin naturally present on the surface of the plant, such lesions, of course, are not formed. However, if the carbon chain is too long, problems of adhesion, compatability and emulsion stability may arise. Therefore, it is desirable to employ a paraffin having a melting point not more than 10° C. higher than the naturally present paraffin.

As the emulsifier, saturated or unsaturated $C_{12}$ to $C_{18}$ fatty acid soaps are employed.

Oleic acid, steric acid and other fatty acids mixed with these acids, are the preferred fatty acids, and these may be saponified with an alkali or alkaline earth metal hydroxide or carbonate, the alkali metal carbonate being preferred.

In order to achieve a stable and effective emulsion, it is preferred to melt the paraffin and fatty acid together and then add an aqueous solution of alkaline substance to the melt under high speed stirring, e.g. at above 80° C. and continue high speed stirring until the emulsion cools to about 60° C. Then the stirring is performed as slowly as possible.

An emulsion concentration of about 30% is the most mobile and effective. Concentrations of more than 40% emulsion are undesirable because of the lack of mobility. Of course, the stability and mobility may vary with the nature of the paraffin emulsifier, conditions such as temperature during emulsification, etc.

The emulsion is diluted with water prior to use.

Furthermore, due to the fact that the emulsion can retain efficacy at 200x dilution with water, it is highly economical.

The instant W/O paraffin emulsions have a particle size of between 1 and 5 microns and exhibit a surface tension of about 36 dynes/cm at 50x dilution with water, about 37 dynes/cm at 100x dilution with water and about 43 dynes/cm at 200x dilution with water.

A wide variety of plants may be suitably treated by the present invention and included among these are vegetable plants such as tomato, cucumber and eggplants, flowering plants such as chrysanthemums and carnations, deciduous fruit trees such as apple, pear and grape. Tea plants, rice plants and numerous others are also satisfactorily treated by the present invention.

The following non-limitative examples will further illustrate the present invention.

COMPARATIVE EXAMPLE

The following emulsion is made in accordance with the teachings of Japanese Pat. No. 46-4964. All percentages are by weight.

A solution containing 67.8% water, 1.2% of potassium carbonate, 25% paraffin, 5% stearic acid and 1% oleic acid is formed by melting the stearic acid, oleic acid and paraffin at about 90° to 100° C. and adding an aqueous solution of the potassium carbonate at 90° to 100° C. The resultant solution is stirred for more than 10 minutes at the temperature of 90° to 100° C. in a mixer at 1500 to 3600 r.p.m. until the apparent volume swells to about twice the original volume. This well stirred solution is cooled to 25° C. under stirring.

The paraffin emulsion produced by this method has a characteristic emulsion particle size of 5 to 10 microns and a surface tension of 38 dyne/cm with 50x dilution with water, 45 dyne/cm with 100x dilution and 47 dyne/cm with 200x dilution. However, despite these advantages, the range of the maximum dilution of this emulsion with retention of efficacy is about 50 to 100x, which is uneconomical.

EXAMPLE OF THE PRESENT INVENTION

A mixture of 30% of paraffin, 5% oleic acid, 1% potassium carbonate and 64% water is stirred at 80° C. to 85° C. for more than 20 minutes by using a high speed mixer 6000 r.p.m. to 8000 r.p.m. The mixer is slowed to the lowest speed when the temperature of this mixture becomes about 60° C. and stirring is stopped when the temperature reaches about 30° C. to 40° C. The particles of paraffin emulsion, produced by this improved method, are small, 1 to 5 microns at the most.

The surface tension of emulsion is also improved, for example 36 dyne/cm with 50x dilution, 37 dyne/cm with 100x dilution and 43 dyne/cm with 200x dilution.

In the present emulsion, the amount of paraffin included in the emulsion is increased by only 5% compared to Japanese application No. 46-4964, yet a 200x dilution with water is made possible without losing efficacy.

Many variations of the foregoing will be apparent without departing from the spirit and intent of the invention.

I claim:

1. A method for protecting plants from diseases caused by airborne carriers which comprises:
    applying to a plant, an effective amount to protect said plants against such airborne diseases, of a W/O emulsion of a hard paraffin having substantially the same number of carbon atoms as that naturally present on the surface of the plant;
    said emulsion being prepared by emulsifying said paraffin with a $C_{12}$ to $C_{18}$ fatty acid soap to produce an emulsion having colloidal particles consisting essentially of those within the range of from 1 to 5 microns;
    said emulsion, after evaporation of water therefrom depositing a block-like film of paraffin on said plant.

2. The method according to claim 1 wherein said emulsion is diluted with water between 50 and 200x prior to application to said plant, said 50x diluted emulsion having a surface tension of 36 dynes/cm and said 200x diluted emulsion having a surface tension of 43 dynes/cm.

3. The method according to claim 2 wherein said emulsion is made by:
    (a) mixing said hard paraffin, $C_{12}$ to $C_{18}$ fatty acid, an alkaline material and water at about 80 to 85° C. to form a solution,
    (b) stirring said solution at 6000 to 8000 r.p.m. on a high speed stirrer until the solution cools to 60° C., then
    (c) slowly stirring until the resultant emulsion cools to 35° to 40° C.

4. The method according to claim 1 wherein the paraffin has between 20 and 35 carbon atoms.

5. The method according to claim 1 wherein the paraffin has between 20 and 25 carbon atoms and melts between 36.8° to 74.7° C.

6. The method according to claim 5 wherein at least 80% of the paraffin is n-paraffin.

7. The method according to claim 1 wherein the fatty acid is stearic acid or oleic acid.

8. The method according to claim 3 wherein the fatty acid is stearic acid or oleic acid.

9. The method according to claim 8 wherein the alkaline material is sodium or potassium carbonate.

10. The method according to claim 2 wherein the emulsion is employed at about 200x dilution.

11. The method according to claim 1 wherein the thickness of the paraffin film, after evaporation of water from the emulsion is 0.8 to 1 micron.

12. The method according to claim 3 wherein in step (a) the fatty acid and paraffin are melted together and said alkaline material is dissolved in said water to form an aqueous solution which is then added to said melt.

13. The method according to claim 9 wherein in step (a) the fatty acid and paraffin are melted together and said alkaline material is dissolved in said water to form an aqueous solution which is then added to said melt.

* * * * *